US011162880B2

(12) United States Patent
Schorey et al.

(10) Patent No.: US 11,162,880 B2
(45) Date of Patent: Nov. 2, 2021

(54) PARTICLE SIZE PURIFICATION METHOD AND DEVICES

(71) Applicant: University of Notre Dame du Lac, South Bend, IN (US)

(72) Inventors: Jeffrey S. Schorey, South Bend, IN (US); Yong Cheng, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 225 days.

(21) Appl. No.: 15/774,972

(22) PCT Filed: Nov. 8, 2016

(86) PCT No.: PCT/US2016/060960
§ 371 (c)(1),
(2) Date: May 9, 2018

(87) PCT Pub. No.: WO2017/083286
PCT Pub. Date: May 18, 2017

(65) Prior Publication Data
US 2019/0011342 A1    Jan. 10, 2019

Related U.S. Application Data

(60) Provisional application No. 62/252,641, filed on Nov. 9, 2015.

(51) Int. Cl.
*G01N 1/40*   (2006.01)
*B01D 61/14*  (2006.01)
*B01D 61/18*  (2006.01)
*B01D 63/08*  (2006.01)
*G01N 33/49*  (2006.01)

(52) U.S. Cl.
CPC ......... *G01N 1/4077* (2013.01); *B01D 61/142* (2013.01); *B01D 61/147* (2013.01); *B01D 61/18* (2013.01); *B01D 63/082* (2013.01); *G01N 33/491* (2013.01); *B01D 2313/143* (2013.01); *B01D 2313/146* (2013.01); *B01D 2319/025* (2013.01); *B01D 2319/06* (2013.01); *G01N 2001/4088* (2013.01)

(58) Field of Classification Search
None
See application file for complete search history.

(56) References Cited

U.S. PATENT DOCUMENTS

| | | | |
|---|---|---|---|
| 5,683,916 | A | 11/1997 | Goffe et al. |
| 2006/0029923 | A1 | 2/2006 | Togawa et al. |
| 2011/0139717 | A1 | 6/2011 | Malenfant et al. |
| 2014/0004601 | A1 | 1/2014 | Lim |
| 2015/0210986 | A1 | 7/2015 | Vicalvi, Jr. et al. |

FOREIGN PATENT DOCUMENTS

| | | |
|---|---|---|
| WO | 2011151314 A1 | 12/2011 |
| WO | 2014140211 A1 | 9/2014 |
| WO | 2014188313 A1 | 11/2014 |
| WO | 2015059714 A1 | 4/2015 |
| WO | 2015137860 A1 | 9/2015 |

OTHER PUBLICATIONS

Hydrophilic Multilayer Durapore 0.45/0.22μm Filter Data Sheet (EMD Millipore Corporation, 2012).*
International Search Report and Written Opinion for PCT/US2016/060960 dated Feb. 20, 2017.
Hong et al., "Plasma exosomes as markers of therapeutic response in patients with acute myeloid leukemia." Frontiers in Immunology, Tumor Immunity, vol. 5, Article 160, Apr. 2014, pp. 1-9.
Hornick et al., "Serum Exosome MicroRNA as a Minimally-Invasive Early Biomarker of AML." Scientific Reports, www.nature.com/ScientificReports, 5:11295, 2015, pp. 1-12.
Manterola et al., "A small noncoding RNA signature found in exosomes of GBM patient serum as a diagnostic tool." Neuro-Oncology, vol. 16, No. 4, 2014, pp. 520-527.
Munson et al., "Exosomes: Potential in Cancer Diagnosis and Therapy." Medicines, vol. 2, 2015, pp. 310-327.
Ogata-Kawata et al., "Circulating Exosomal microRNAs as Biomarkers of Colon Cancer." PLOS One, vol. 9, No. 4, e92921, Apr. 2014, pp. 1-9.
Properzi et al., "Exosomes: the future of biomarkers in medicine." Biomarkers in Medicine, vol. 7, No. 5, 2013, pp. 769-778.
Kourembanas, Stella, "Exosomes: vehicles of intercellular signaling, biomarkers, and vectors of cell therapy." Annual Review of Physiology, vol. 77, 2015, pp. 13-27.
Taylor et al., "MicroRNA signatures of tumor-derived exosomes as diagnostic biomarkers of ovarian cancer." Gynecologic Oncology, vol. 110, No. 1, Jul. 2008, pp. 13-21.
"Exosomal microRNAs step into the biomarker arena" Gynecologic Oncology, vol. 110, 2008, pp. 1-2.

* cited by examiner

*Primary Examiner* — Brian Gangle
(74) *Attorney, Agent, or Firm* — Haukaas Fortius PLLC; Michael H. Haukaas

(57) ABSTRACT

A particle separation multi-membrane matrix device and method are provided. The particles isolated may comprise nano-scale particles, such extracellular membrane vesicles, having a size of about 50 to about 150 nm. The vesicles are released by many different cell types, and may be efficiently isolated at high yield and purity according to the present methods from various body fluids (e.g., blood, saliva, breast milk, serum, plasma, ascites fluid, etc.). Such isolated exosome preparations may include biomarkers, such as disease biomarkers (diagnostic markers) for various disease (early stage and late stage cancers, neurological disorders (Parkinson disease, Alzheimer disease), diabetes, pancreatic diseases, renal failure, infectious diseases (HIV, tuberculosis, malaria, hepatitis)). The present methods and devices may be used to detect and monitor animals (human, livestock, companion animal) for infectious diseases, such as tuberculosis and other diseases. The methods and devices require minimal sample material (10 μl), are rapid, economical, yield highly enriched small molecule (eg, exosomes) preparations, and do not require electricity.

19 Claims, 12 Drawing Sheets

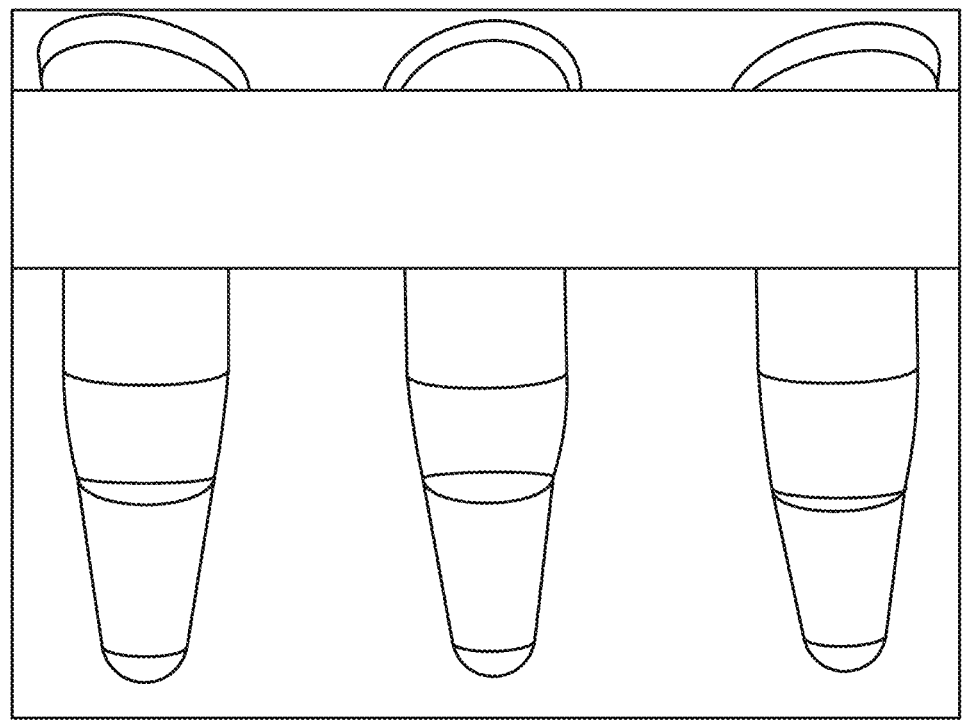
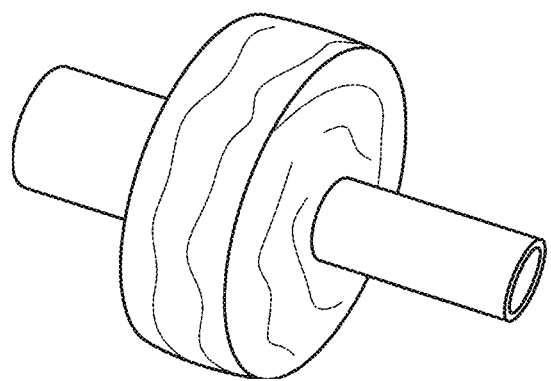
FILTER
*Fig. 3*

Determination of ExoPen-based Human Serum Exosome Purification Efficiency in comparison with EXOQUICK product-based Exosome Isolation.

Materials:
10 TB patient serum samples (20 tubes) from CSU
Methods:
1) ExoPen
2) EXOQUICK product
3) NANOSIGHT product
4) BCA test
5) Ultracentrifuge
6) SDS-PAGE analysis and Coomassie staining

Results
1) Coomassie-stained SDS-PAGE Gel
2) Particle Abundance
3) Protein Abundance

*Fig. 5*

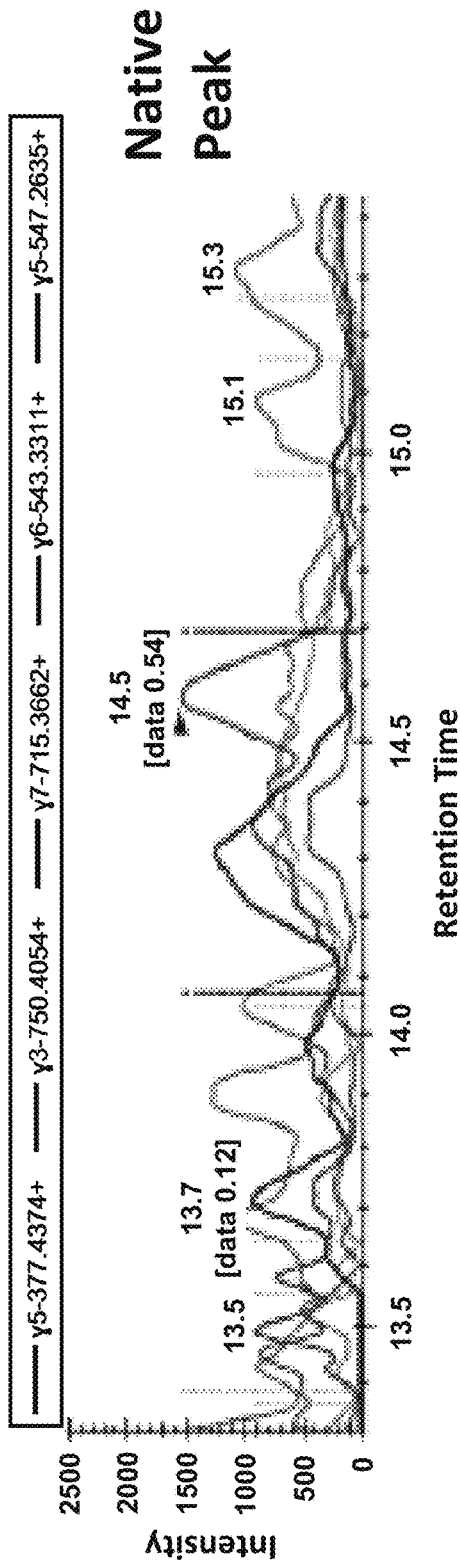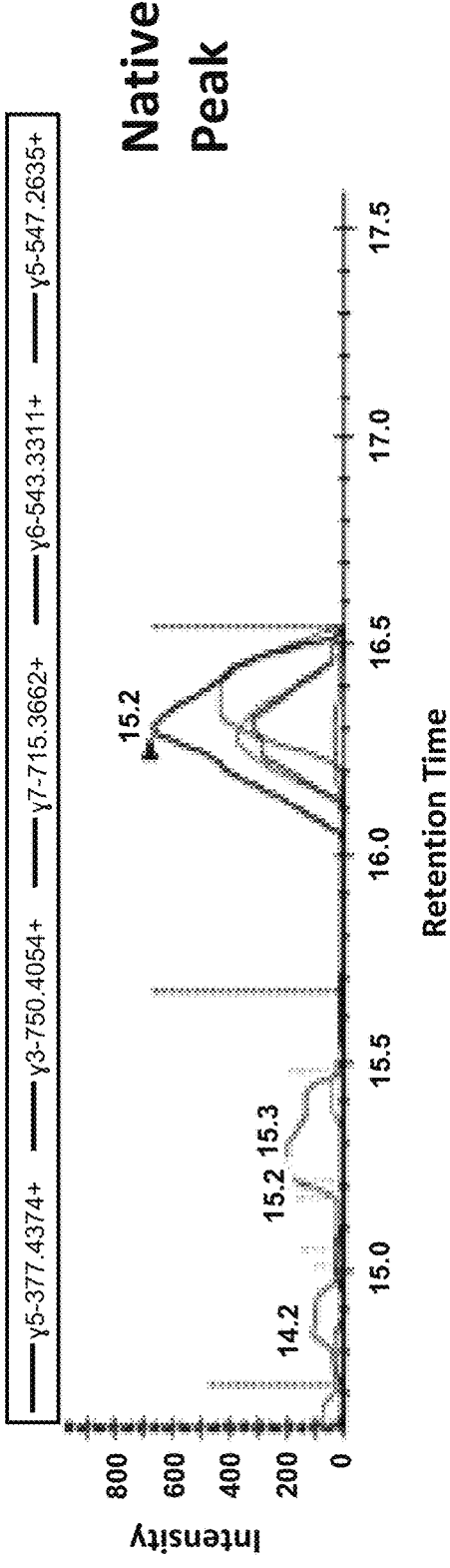
Fig. 11

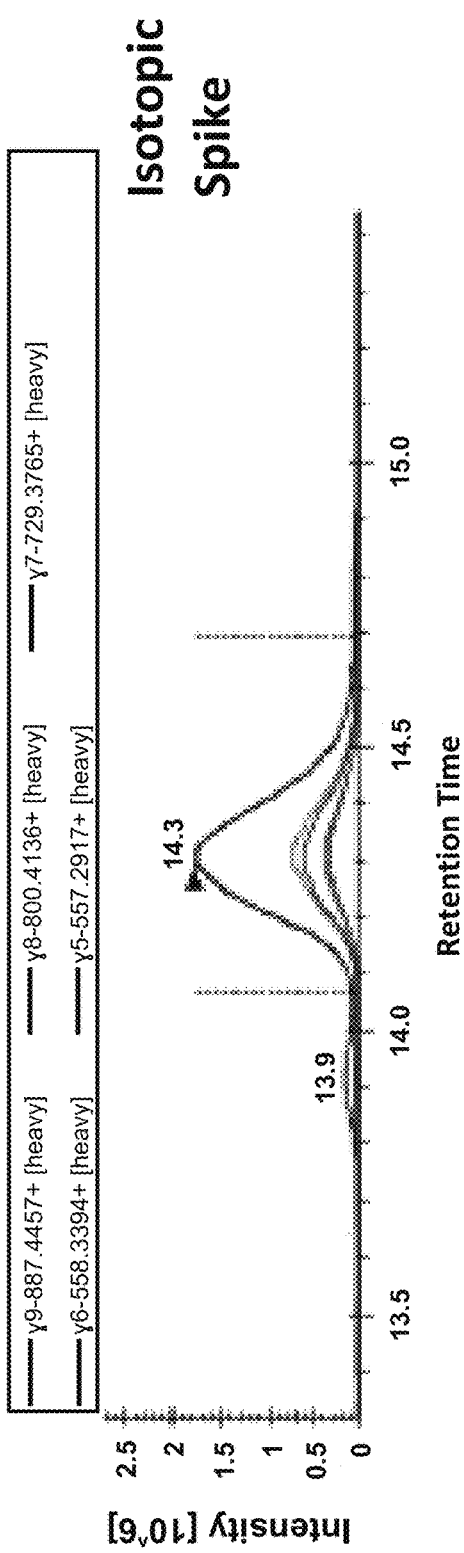
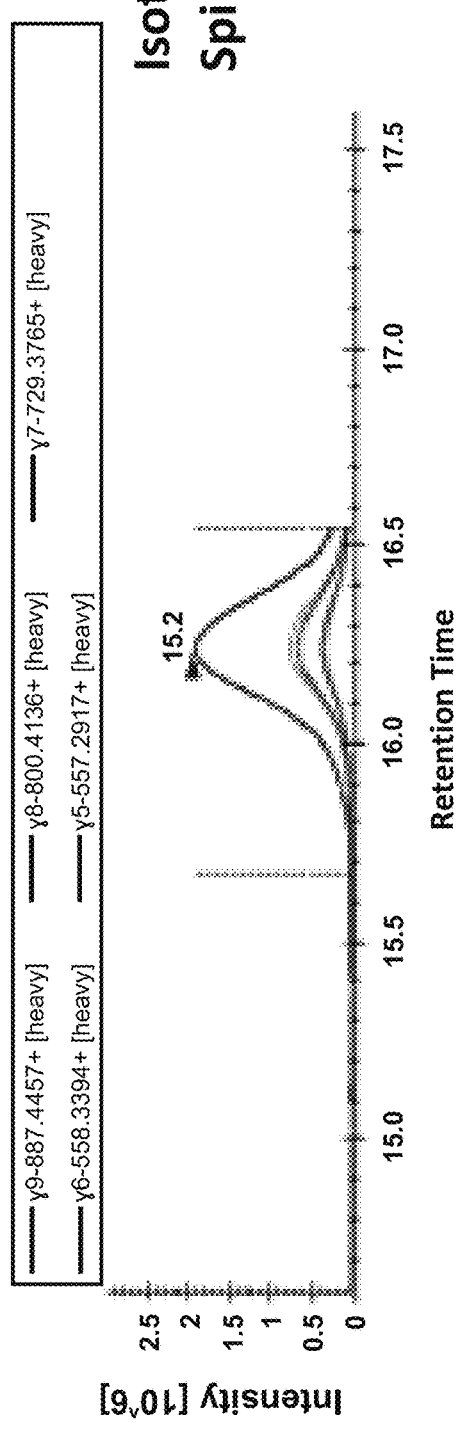
Fig. 11 (cont.)

ExoPen vs EXOQUICK product (Mass Spectrometric Analysis)

| *Mycobacterium tuberculosis* Peptide | *Mycobacterium tuberculosis* Protein | ExoPen (Better) | EXOQUICK product (Better) | Tie (ExoPen vs EXOQUICK product) | Tuberculosis Patient ID |
|---|---|---|---|---|---|
| FLE | Ag85c | 50% | 0 | 50% | 11 |
| LYA | Mpt32 | NA | NA | NA | 12 |
| EAL | BfrB | 50% | 0 | 50% | 7 |
| AGA | BfrB | 33% | 33% | 33% | 7 |
| GSL | Cfp2 | 60% | 0 | 40% | 12 |
| DVL | GroEL | 60% | 40% | 0 | 1 |
| SLE | Mpt64 | 50% | 50% | 0 | 11 |
| FLS | Mpt64 | 100% | 0 | 0 | 11 |
| ITQ | DnaK | 0 | 0 | 100% | 11 |

*Fig. 12*

PARTICLE SIZE PURIFICATION METHOD AND DEVICES

CROSS-REFERENCE TO RELATED APPLICATIONS

The present application claims priority to U.S. Ser. No. 62/252,641, filed Nov. 9, 2015, the entire contents of which are specifically incorporated herein by reference in its entirety.

STATEMENT REGARDING FEDERALLY SPONSORED RESEARCH OR DEVELOPMENT

None

FIELD OF THE INVENTION

This invention relates to the field of methods for screening biological fluids for biomarkers, such as biomarkers for disease, as well as devices for screening biological fluids and isolating materials from a biological fluid, such as exosomes.

BACKGROUND OF THE INVENTION

The selection of particular particles of interest from a sample, such as from a biological sample, presents several challenges related to yield and purity. Virtually all existing techniques require some form of sophisticated laboratory equipment, electricity source, and a more than a minimal volume of a sample to provide.

Exosomes are nano-scale extracellular membrane vesicles of 50 to 150 nm, released by most cell types within multicellular organisms including humans. These vesicles may be detected in various body fluids including blood, saliva, breast milk, etc. A number of studies indicate that exosomes isolated from serum of diseased individuals carry specific molecules that may serve as diagnostic biomarkers for the specific disease. These diseases include cancers, Neurological disorders such as Parkinson disease and Alzheimer disease, diabetes, pancreatic diseases, renal failure, infectious diseases such as HIV, tuberculosis, malaria and hepatitis, as well as other diseases. Exosome-based noninvasive diagnostic technology has a priority for the diseases such as early stage cancers which are difficultly to detect by traditional methods. For infectious diseases such as tuberculosis, exosomes may decrease the cost and simplify the diagnosis process allowing for wider use in areas of limited resources.

The substantial increase in exosome research and their potential use clinically has attracted the attention of numerous companies, especially those in the field of diagnostics. These companies include Qiagen and Thermo Fisher Scientific; two of the largest companies in the world making biotechnology products. However, the current commercial kits/reagents for exosome purification are based on non-specific precipitation using polymers, size exclusion chromatography or antibody-based affinity purification. These approaches suffer various disadvantages, including high background readings that distort results and mask detection of the diagnostic molecule of interest in a sample (soluble protein/component contamination in the final preparation) or in the case of an antibody-based approach, the cost of the reagents and the necessity that the exosome contain the antigen recognized by the antibody.

A need continues to exist in the medical arts for disease diagnosis that is noninvasive, accurate, quick, requires minimal material, and that may be used to detect disease using a wide variety of body fluids.

SUMMARY OF THE INVENTION

In a general and overall sense, methods and devices for selecting for particles having a defined size of about 50 to about 200 nm, using a multi-membrane device.

In some embodiments, the particles comprise biostructures, such as exosomes.

In other embodiments, the particles comprise exosomes that comprise a particular biomarker of interest in a biological fluid sample (such as serum).

in other embodiments detecting informative biological markers associated with disease are provided. The methods and tools identify informative disease biomarkers in a sample through analysis of a specialized group of biostructures present in a biological fluid, called exosomes.

Methods for preparing an enriched preparation of exosomes in a biological fluid are also provided. The present methods and tools may be used to isolate exosomes and detect disease markers in virtually any body fluid, regardless of the species of origin (human, mouse, rat, rabbit, cow, etc.).

It is envisioned that the methods and tools may be used in both laboratory research settings as well as in commercial diagnostic applications, such as part of a clinical exosome-based diagnostic system, combined with a disease—specific biomarker detection platform. In this regard, the present methods and devices may be used for detection of any number of different diseases having a biomarker. For example, an exosome (extracellular vesicles) preparation for a biological fluid, such as extracellular vesicles purified from serum or plasma, may be used in the diagnosis of various diseases. These diseases include tuberculosis, colon cancer, acute myeloid leukemis (AML), glioblastoma multiforme (GBM), ovarian cancer, and others.

The methods and devices described herein provide a combined filtration and size-exclusion purification technique, whereby particles and proteins having a size greater than 220 nm and less than 700 Daltons are removed. In relation to a biological fluid, such as a blood, serum, plasma, or ascites fluid sample, a processed preparation using the presently described devices and/or according to the present methods may include any or all of the following molecules.

| | |
|---|---|
| HDL | Size: 5 to 15 nm |
| LDL | Size: 18 to 28 nm |
| IDL | Size: 25 to 50 nm |
| VLDL | Size: 30 to 80 nm |
| Chylomicrons | Size: 100 to 1000 nm |

*Total concentration in blood: $1 \times 10(3)$ to $1 \times 10(4)$ g/ml

In some aspects, the invention may be described as a n exosome-based disease diagnosis method.

In another aspect, the invention provides an exosome purification process/tool. The advantages of these processes/tools include that it provides an analysis quickly, requires a relatively small amount of sample biological fluid/test material, and may be used with a variety of body fluids, including urine, blood, serum, plasma, saliva, mucus, and other biological fluids.

BRIEF DESCRIPTION OF THE DRAWINGS

FIG. 1 is Body fluid is passed through a filter consisting of multiple membranes (80 µm, 10 µm and 0.2 µm filter membranes in series). To make this multi-membrane unit, a 0.2 μm filter unit is separated and additional filters are added on top of the 0.2 μm membrane divided spatially by thin washers (see figure). The whole filter is glued together to produce a multi-membrane filter unit. This allows the void volume to be kept at a minimal as fluid is pushed through.

FIG. 3 are slide pictures of the material that would constitute an ExoPen including the filters. FIG. 3 is the 80 μm (Millipore, Ref No. NY8002500), the 10 μm (GVS Maine Magna, Ref No. R99SP02500) of the Exopen. The 0.2 μm (Millipore, Ref. No. SLLGH13NL) filter membranes in series) of the Exopen. The CAPTO Core 700 beads. These beads are placed in the column (Capacity, 23.4 mg; Void volume, 600 ul), and the column is then equilibrated with 10 ml of washing buffer (PBS with 0.05% TWEEN-80 product (PBST).

FIG. 5—a list of reagents and samples used along with the type of analysis performed on the 10 human serum samples from Tuberculosis patients.

FIG. 7A shows certain proteins co-purify with isolated exosomes from human serum using the ExoPen column. FIG. 7B shows certain proteins co-purify with exosomes using the EXOQUICK product. For EXOQUICK product, we followed manufactures protocol for precipitation of exosomes. The gel in FIG. 7B shows a significant number of proteins in the dissolved EXOQUICK product pellet. Most of these proteins were just "trapped" in the precipitant when using EXOQUICK product and are not attached/imbedded in the exosome. That is, these proteins are contaminates co-purified with the exosomes.

FIG. 10 A—EXOQUICK product—most of the protein pulled down by the EXOQUICK product was just contaminants. Even the protein brought down by the centrifugation was likely, in part, protein aggregates also brought down by the EXOQUICK product. 10B—ExoPen purified vesicles isolated in pellet. All the protein isolated with the ExoPen was associated with the pellet vesicles. The use of ExoPen resulted in a much purer preparation of exosomes.

FIG. 11A and FIG. 11B: The purified exosomes were subjected to a digestion to digest Mpt64 protein Mpt64 protein is present on the surface of exosomes. The digested exosome material was subjected to Mass Spec. analysis. The digested material was analyzed for the presence of four (4) peptides identified from the digestion of the mycobacterial protein Mpt64. In FIG. 11A, the two MS spectra present the results of the 4 peptides used for analyzing for the presence of Mpt64 in the samples. In FIG. 11B, the spectra was much cleaner when the ExoPen purified sample was used. The two spectra: injection of synthesized peptide FLS (i.e. positive control) which allowed for visualization of peptide retention times.

FIG. 12: ExoPen vs EXOQUICK product Mass Spectrometric Analysis of human tuberculosis patient serum sample content of *Mycobacterium tuberculosis* peptides (9 peptides) and *Mycobacterium tuberculosis* proteins (9 peptides).

DETAILED DESCRIPTION OF THE PREFERRED EMBODIMENT

Figure 1:
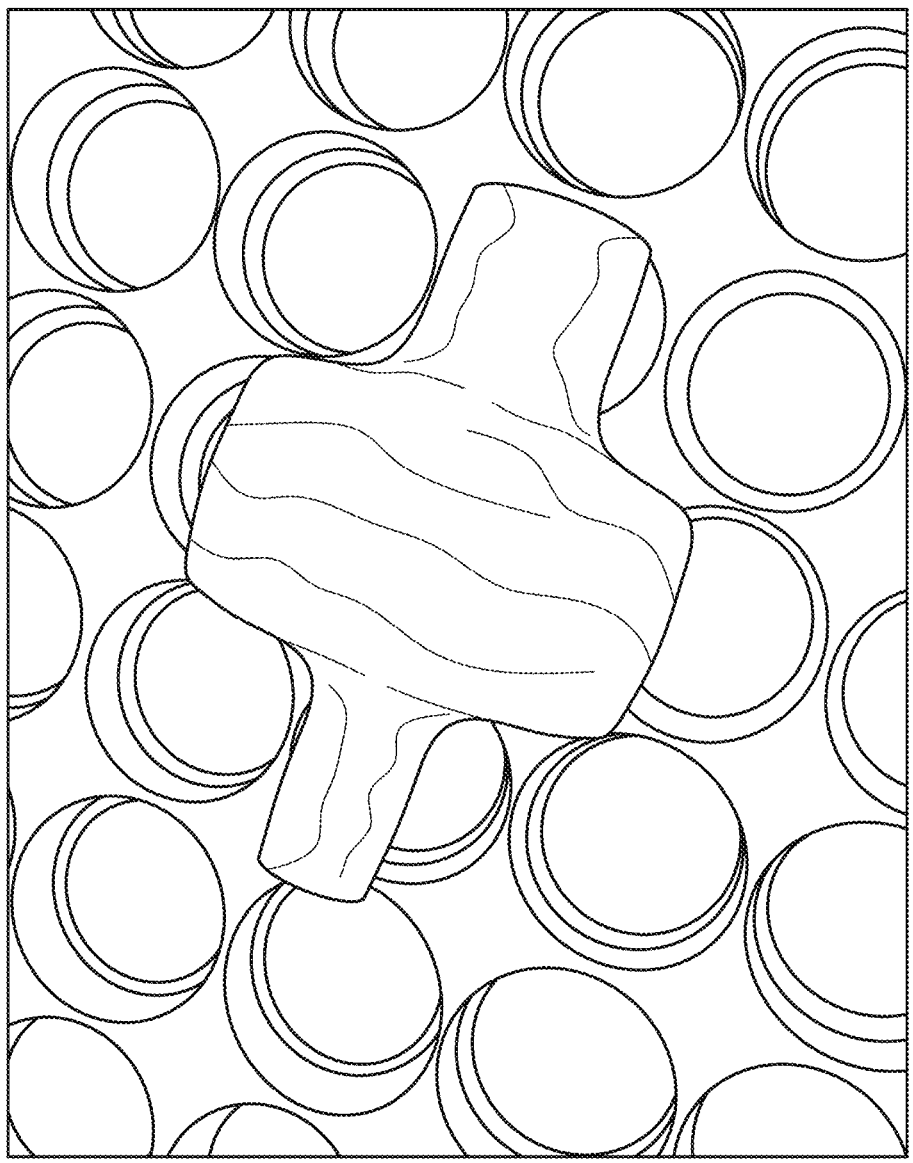

Throughout the specification and claims, the following terms take the meanings explicitly associated herein, unless the context clearly dictates otherwise.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, the term "or" is an inclusive "or" operator and is equivalent to the term "and/or" unless the context clearly dictates otherwise.

The term "based on" is not exclusive and allows for being based on additional factors not described, unless the context clearly dictates otherwise.

The term "a," "an," and "the" include plural references. Thus, "a" or "an" or "the" can mean one or more than one. For example, "a" cell and/or extracellular vesicle can mean one cell and/or extracellular vesicle or a plurality of cells and/or extracellular vesicles.

The meaning of "in" includes "in" and "on."

As used herein, the terms "administering", "introducing", "delivering", "placement" and "transplanting" are used interchangeably and refer to the placement of the extracellular vesicles of the technology into a subject by a method or route that results in at least partial localization of the cells and/or extracellular vesicles at a desired site. The cells and/or extracellular vesicles can be administered by any appropriate route that results in delivery to a desired location in the subject where at least a portion of the cells and/or extracellular vesicles retain their therapeutic capabilities. By way of example, a method of administration includes intravenous administration (i.v.).

As used herein, the term "treating" includes reducing or alleviating at least one adverse effect or symptom of a disease or disorder through introducing in any way a therapeutic composition of the present technology into or onto the body of a subject.

As used herein, "therapeutically effective dose" refers to an amount of a therapeutic agent (e.g., sufficient to bring about a beneficial or desired clinical effect). A dose could be administered in one or multiple administrations (e.g., 2, 3, 4, etc.). However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., cells and/or extracellular vesicles as a pharmaceutically acceptable preparation) for aggressive vs. conventional treatment.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "pharmaceutical preparation" refers to a combination of the A1 exosomes, with, as desired, a carrier, inert or active, making the composition especially suitable for diagnostic or therapeutic use in vitro, in vivo, or ex vivo.

As used herein, the terms "pharmaceutically acceptable" or "pharmacologically acceptable" refer to compositions that do not substantially produce adverse reactions, e.g., toxic, allergic, or immunological reactions, when administered to a subject. For example, normal saline is a pharmaceutically acceptable carrier solution.

As used herein, the terms "host", "patient", or "subject" refer to organisms to be treated by the preparations and/or methods of the present technology or to be subject to various tests provided by the technology.

The term "subject" includes animals, preferably mammals, including humans. In some embodiments, the subject is a primate. In other preferred embodiments, the subject is a human.

As used herein, the term "treating" includes reducing or alleviating at least one adverse effect or symptom of a disease or disorder through introducing in any way a therapeutic composition of the present technology into or onto the body of a subject.

As used herein, the term "effective amount" refers to the amount of a composition sufficient to effect beneficial or desired results. An effective amount can be administered in one or more administrations, applications or dosages and is not intended to be limited to a particular formulation or administration route.

The term "subject" includes animals, preferably mammals, including humans. In some embodiments, the subject is a primate. In other preferred embodiments, the subject is a human.

It is specifically intended that the present invention not be limited to the embodiments and illustrations contained herein, but include modified forms of those embodiments including portions of the embodiments and combinations of elements of different embodiments as come within the scope of the following claims.

The following examples are provided to demonstrate and further illustrate certain preferred embodiments and aspects of the present technology, and they are not to be construed as limiting the scope of the technology.

Example 1—Multimember Filter Unit

The present example details a specific configuration of the multimember filter unit that is included in the particle size separation device. The particle size separation device is referred to herein as an "ExoPen".

Figure 4:
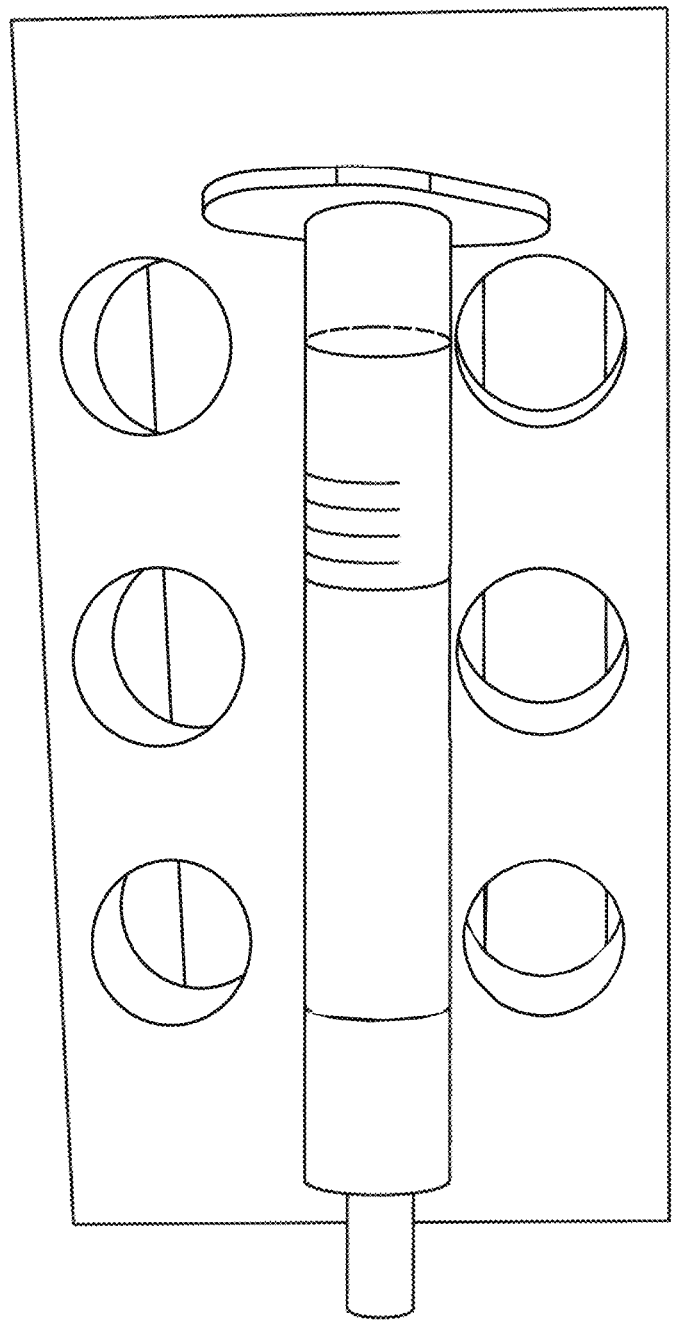
FIG. 4—The Exopen column.

The multimember filter unit comprises multiple membranes, these membranes having very small pore sizes, and are configured as part of the present separation device in a series of membranes having decreasing pore sizes. For example, a membrane providing a 80 µm filter, a membrane providing a 10 µm filter and a membrane providing a 0.2 µm filter, in series, will be assembled as part of one configuration. In addition, to make this multi-membrane unit, the 0.2 µm filter unit is separated and additional filters are added on top of the 0.2 µm filter membrane, these filter membranes being divided spatially by thin washers (see FIG. 3). The whole multi-filter construct is glued together to produce a multi-membrane filter unit (FIG. 4).

The configuration of the multi-membrane unit allows the void volume to be kept at a minimal as fluid is pushed through.

FIG. 3 presents a depiction of the multi filter unit in the described ExoPen device. The filter unit includes the series of micro-filters described above, 80 µm (Millipore, Ref No. NY8002500), 10 µm (GVS Maine Magna, Ref. No. R99SP02500) and 0.2 µm (Millipore, Ref. No. SLLGH13NL) filter membranes in series, and CAPTO Core 700 beads in a column configured cylinder (Capacity, 23.4 mg; Void volume, 600 ul). This particular size column will be equilibrated with 10 ml of a washing buffer (PBS-T).

It is envisioned that larger volume columns or smaller volume columns may be constructed according to the present invention to suit any specific application needed for isolation of particles within a sample.

Example 2—Method of Exosome Purification

The present example presents a description of a method of isolating and/or providing a purified preparation of exosomes from a biological fluid using the multi-filter unit described above, such as in an ExoPen construct.

A biological fluid, such as a body fluid (serum, blood, plasma, ascites fluid) is passed through a multi-membrane filter unit (See filter depicted at FIG. 1). Any remaining biological fluid contained within the filter unit is collected by adding PBST to the filter unit and is collected as the PBST buffer is being pushed into the membrane unit.

Figure 2:
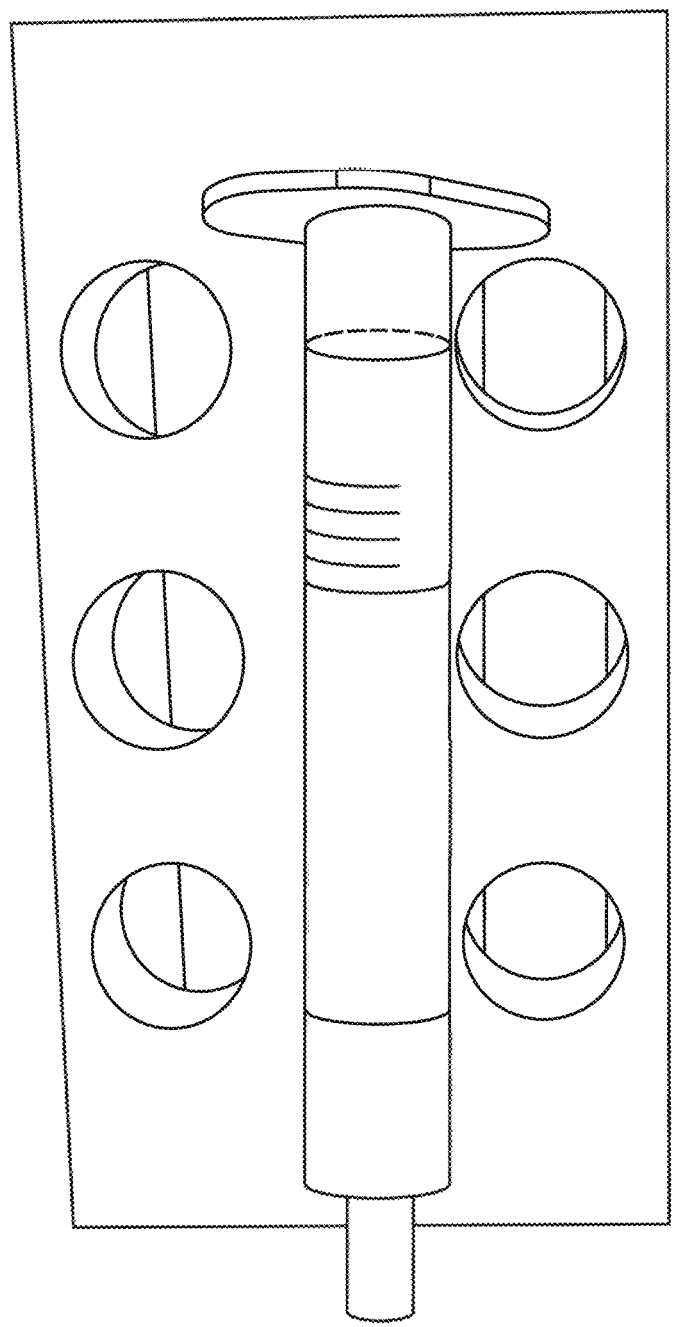
FIG. 2 is a column prepared using a plastic hollow cylinder with a mesh at one end that is used to hold the resin within the cylinder. Load resin possessing an activated core and inactive shell such as GE CAPTO Core 700 beads into the column and equilibrate the column with 10 ml of washing buffer (PBS with 0.05% TWEEN-80 product).

A column (FIG. 2) was prepared using a plastic hollow cylinder with a mesh at one end that was used to hold a resin within the cylinder. GE CAPTO Core 700 beads are loaded into the column and equilibrated with 10 ml of washing buffer (PBST).

The filtered body fluid, which contains free protein and vesicles smaller then 200 nm, was loaded onto the equilibrated column, and then washing buffer was added after all of the body fluid sample entered the resin bed. The volume of sample and wash buffer should be equivalent to the void volume of the resin. The amount of resin used will depend on the amount of protein within the sample. Small molecules (including proteins) within the filtered body fluid (such as serum) are accessible to the activated core of the resin, and these small molecules become trapped by the resin. Highly enriched exosomes may then be collected from the column in the flow-through.

The first fraction (void volume of the resin bed) will be discarded.

The second fraction is expected to contain purified exosomes. This fraction is used to provide a preparation comprising purified exosomes. These purified exosomes may be used in any variety of products (such as in a therapeutic pharmaceutical preparation) or in subsequent studies. The purified exosomes can be stored at −80° C. until use with preserved activity, or may be used immediately.

Example 4—Materials and Methods

The present example provides the materials and methods (flow chart) by which a sample may be processed to isolate by particular size, the various components in the sample. In this example, a human serum is the fluid examined. The particles being isolated are exosomes.

FIG. 5 presents a list of the types of methods employed in the analysis of a sample in assessing exosome purification efficiency employing both an ExoPen-based or EXOQUICK product-based exosome purification of a 10 human serum samples obtained from patients with a confirmed tuberculosis disease.

Figure 6:
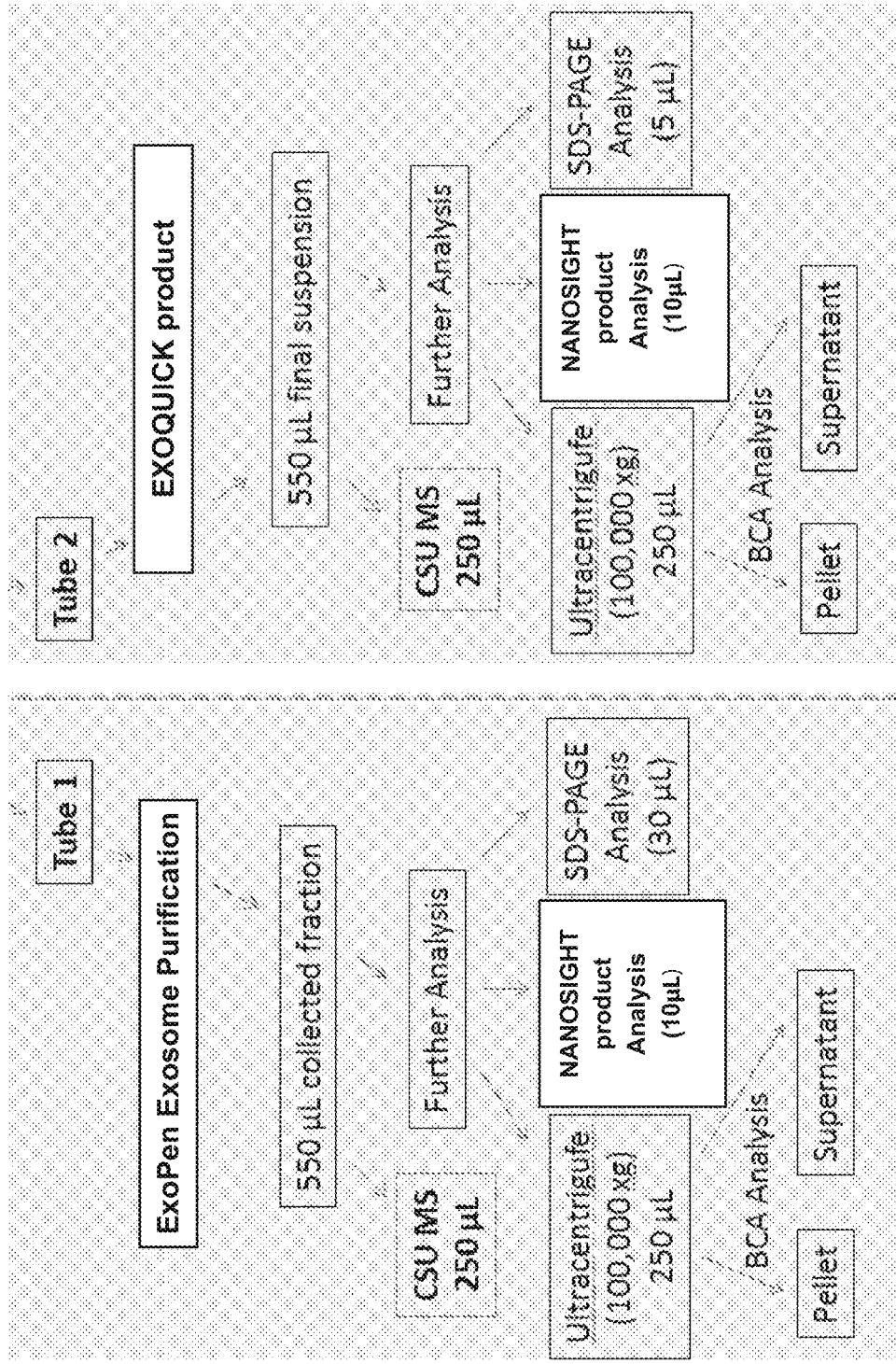
FIG. 6—a workflow chart for processing a biological sample, such as a human serum sample.

FIG. 6 provides a flow-chart of the workflow procedure for processing the human serum samples via either the ExoPen method (Tube 1) or the EXOQUICK product method (Tube 2).

Figure 7:
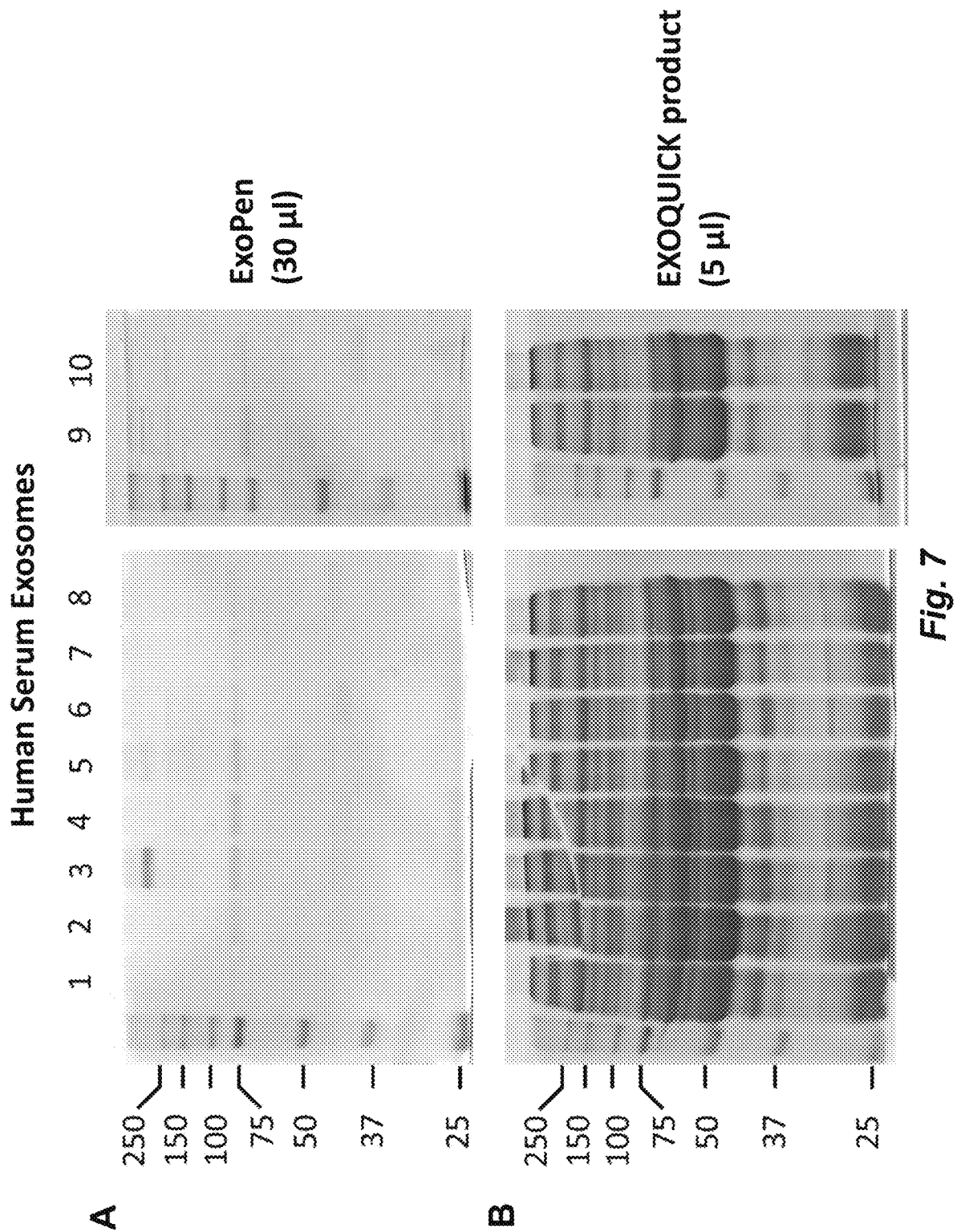
FIG. 7A and FIG. 7B—Gel analysis of exosomes purified by ExoPen and EXOQUICK product.

EXOQUICK product reagent is added to serum at a 4:1 ratio (25 µl EXOQUICK product per 100 µl of serum). The sample is mixed and kept on ice for a minimal of 1 hour but can be kept at 4° C. overnight. The sample containing the vesicles trapped in a matrix is subject to centrifugation at 1,500×g for 30 minutes at 4° C. to pellet the precipitant. The precipitated matrix is dissolved in an appropriate buffer which in our studies was PBS to release the trapped vesicles Example 5—Gel Analysis of Purity of Isolated Preparations FIG. 7 provides a gel analysis of exosomes purified by use of an ExoPen system compared to the use of an EXOQUICK product system.

The EXOQUICK product system was conducted following the manufactures protocol for precipitation of exosomes.

The gel shows a significant number of proteins in the dissolved EXOQUICK product pellet. As shown in FIG. 7B, most of the proteins were "trapped" in the precipitant using the EXOQUICK product method, and the proteins were not attached/imbedded in the exosome. From this, it was deduced that these proteins were contaminates in the sample.

In contrast, and as shown in the gel provided at FIG. 7A, the proteins were attached to the exosomes eluted. The minimal amount of protein bands observed on the SDS PAGE gel is expected since based on the protein quantitation we loaded less than 1 µg of protein per lane.

Example 6—Particle Abundance Determined by NANOSIGHT Product Analysis in Purified Samples Obtained Using EXOQUICK Product Vs ExoPen The present example demonstrates the number of particles quantified by NANOSIGHT product present in a preparation of a biological fluid (serum) separated using an ExoPen compared to number of particles detected in a sample using EXOQUICK product.

Total particle number in the purified samples. Although the total # was higher for the EXOQUICK product purification for each of the 10 samples, it is likely that some of these particles are protein aggregates which have a size of exosomes (~50 nm). This is also suggested by the very high concentration of protein in the EXOQUICK product samples relative to the ExoPen (~1,000 fold higher) which is not reflected in the difference in vesicle concentration (~3 fold higher on average).

Figure 8:
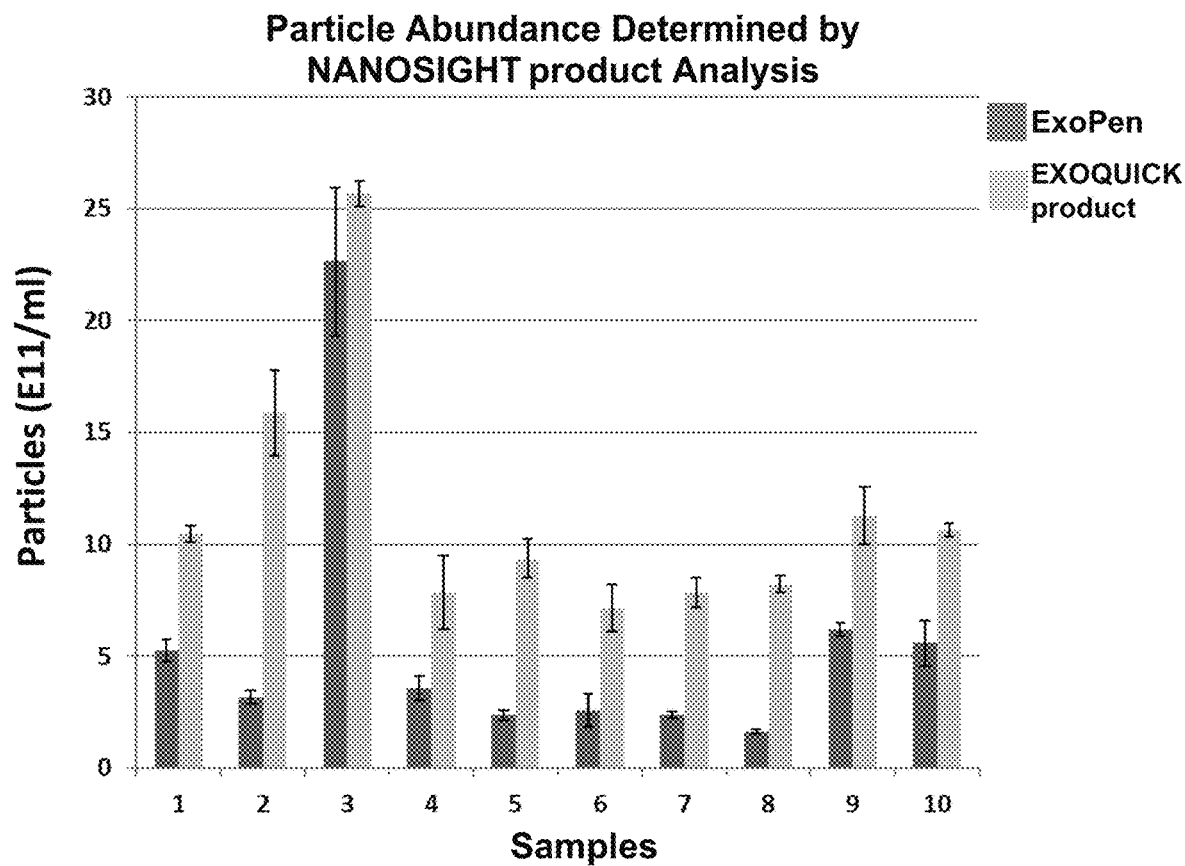
FIG. 8—Total particle number in the purified samples. Although the total # was higher for the EXOQUICK product purification for each of the 10 samples, it is likely that some of these particles are protein aggregates which have a size of exosomes (~50 nm). This is also suggested by the very high concentration of protein in the EXOQUICK product samples relative to the ExoPen (~1,000 fold higher) which is not reflected in the difference in vesicle concentration (~3 fold higher on average).
Figure 9:
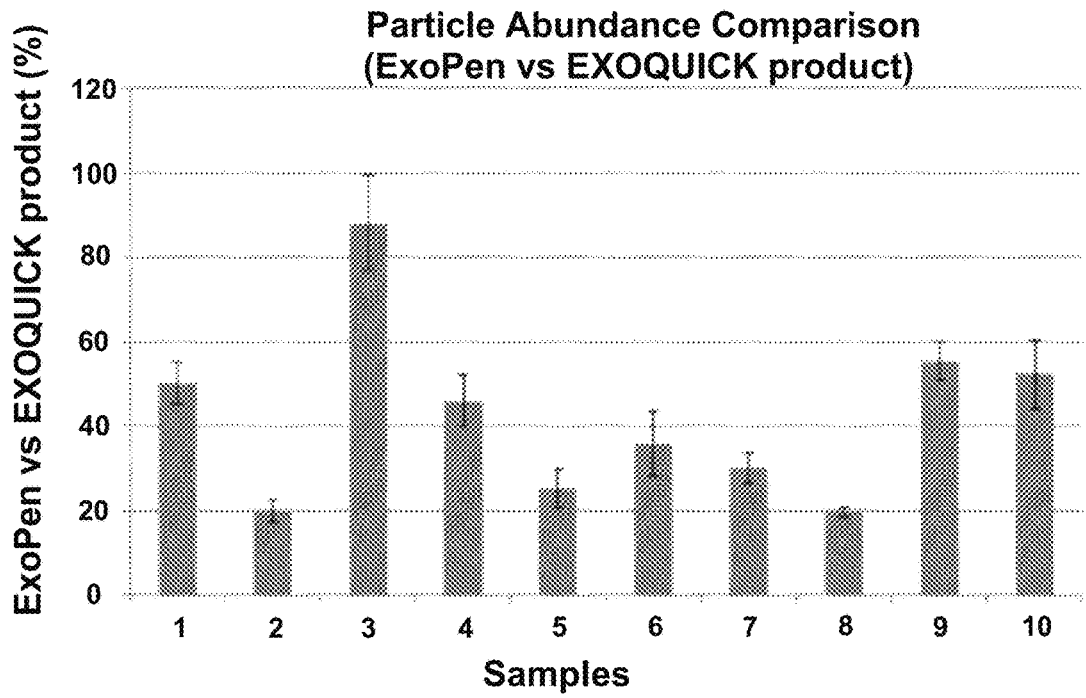
FIG. 9—Percent of vesicles define by NANOSIGHT product using the ExoPen compared to EXOQUICK product.

FIG. 8 shows the percent of vesicles define by NANOSIGHT product for ExoPen purified compared to EXOQUICK product.

Example 7—Protein Abundance Determined by BCA, ExoPen Vs EXOQUICK Product

Figure 10:
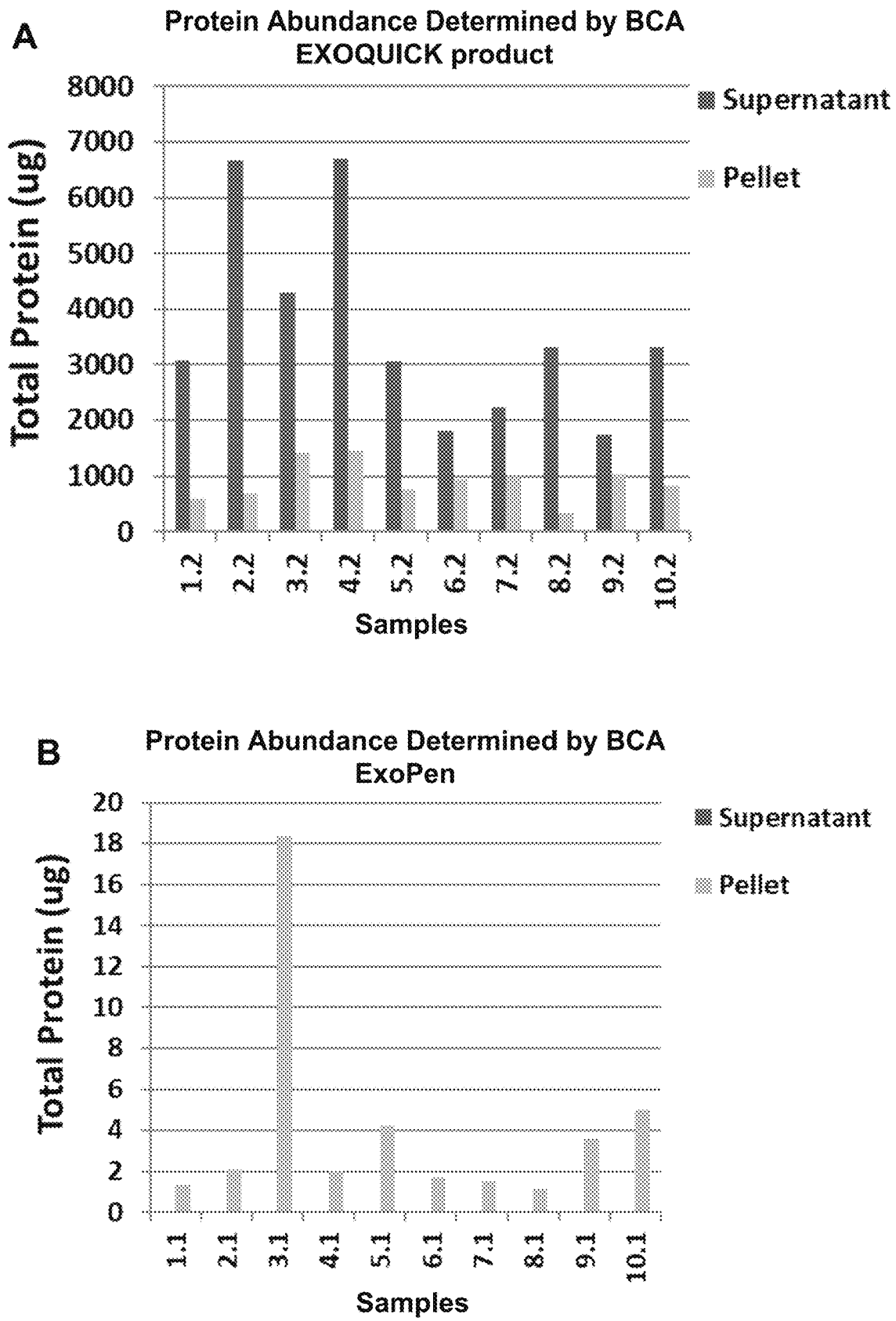
FIG. 10 A-10B—Protein abundance determined by BCA. Prepared human serum exosome samples (250 ul) were ultracentrifuged at 100,000×g, 1 h, 4° C. The supernatant was collected and pellet was resuspended in 50 μl PBS (EXOQUICK product) or PBST (ExoPen). The protein concentration was determined by BCA measurement.

Prepared human serum exosome samples (250 ul) were ultracentrifuged at 100,000×g, 1 h, 4° C. The supernatant was collected and pellet was resuspended in 50 µl PBS (EXOQUICK product) or PBST (ExoPen). The protein concentration was determined by BCA measurement. FIG. 10 A—EXOQUICK product—most of the protein pulled down by the EXOQUICK product was just contaminants. Even the protein brought down by the centrifugation was likely, in part, protein aggregates also brought down by the EXOQUICK product.

FIG. 10B—ExoPen purified vesicles isolated in pellet. All the protein isolated with the ExoPen was associated with the pellet vesicles. The use of ExoPen resulted in a much purer preparation of exosomes.

As shown in FIG. 10, most of the protein pulled down by the EXOQUICK product (FIG. 10A) was contaminant. The protein brought down by the centrifugation was likely, in part, protein aggregates also brought down by the EXOQUICK product.

In contrast, for the ExoPen, all the protein was associated with the pellet vesicles. As shown in FIG. 10B, the use of ExoPen resulted in a much purer preparation of exosomes compared to the EXOQUICK product.

Example 8—EXOQUICK Product Vs ExoPen—Protein: Mpt64 Peptide: FLS

Exosomes isolated according to the present method with the Exopen or EXOQUICK product were subjected to Mass Spec analysis and compared.

The Mpt64 protein, a mycobacterial protein, was used in the present study.

Digested exosome material obtained from two different procedures was examined by Mass Spec. Each of the two digested exosome material was analyzed for the presence of the mycobacterial protein Mpt64. To test for the presence of Mpt64, the exosomes were first treated with trypsin to digest the protein present on/in exosomes. The digestion of the protein was found to yield four (4) identifiable peptides. A preparation of digested exosome material was prepared from the exosomes obtained from each of the two exosome purification techniques. Each of the digested exosome preparations was injected into the Mass Spec instrument, and analyzed. The presence of these 4 peptides derived from digested Mpt64 was determined.

FIG. 11A, top two spectra, demonstrate the results obtained from the analysis of the digested exosome material obtained from each of the two different exosome purification techniques. As can be seen, the Mass Spec peptide analysis results using the EXOQUICK product process was significantly less clear, or "clean", as compared to the peptide analysis by Mass Spec results of the digested exosome material obtained with the ExoPen purified exosome material. MS spectra of the 4 peptides which were used for analyzing for the presence of Mpt64 in the samples. The spectra was much cleaner when the ExoPen purified sample was used.

FIG. 11B, bottom two spectra: injection of synthesized peptide, FLS (i.e. positive control) which allowed for visualization of peptide retention times.

FIG. 12 provides a comparison of results achieved using the Exopen system, and with the EXOQUICK product system, and compares 9 different *Mycobacterium tuberculosis* peptides, and 9 different *Mycobacterium tuberculosis* proteins, in 9 different serum samples (10 µl), isolated from human patients with tuberculosis. These results demonstrate that analysis of the samples using the ExoPen system was significantly better for most of the proteins and peptides examined by Mass Spectrometric analysis.

Example 9—Diseases Detectable with Exosomes Separated by Particle Size (ExoPen)

The present example presents examples of diseases that may be detected using biological samples obtained using the isolation techniques of the ExoPen.

Serum/plasma exosomes as biomarkers for human diseases is described in Properzi et al., 2013, Kourembanas, 2015 and Munson and Shukla, 2015.

Exosomes have been used to detect disease biomarkers for tuberculosis, colon Cancer (Ogata-Kawata et al., 2014), Acute Myeloid Leukemia (AML) (Hong et al., 2014; Hornick et al., 2015), Glioblastoma multiforme (GBM) (Manterola et al., 2014), and ovarian cancer (Taylor et al., 2008). It is anticipated that disease detection for these and other diseases may be accomplished with much smaller patient sample sizes, and much more accurately than previously available techniques, including by an EXOQUICK product technique.

It is specifically intended that the present invention not be limited to the embodiments and illustrations contained herein, but include modified forms of those embodiments including portions of the embodiments and combinations of elements of different embodiments as come within the scope of the following claims.

BIBLIOGRAPHY

The following references are specifically incorporated herein by reference.
1. US 20150210986—Virus purification and formulation process.
2. WO 2015059714 A1—Emergency mode in a hybrid vehicle.
3. WO 2015137860 A1—Separation matrices for purification of biological particles.
4. WO 2014140211 A1—Rna purification methods.
5. US 20150037873 A1—Method for endotoxin removal.
6. WO 2014188313 A1—Purification of polysaccharide protein conjugates.
7. Hong C S, Muller L, Whiteside T L, Boyiadzis M (2014), Front Immunol 5: 160.
8. Hornick N I, Huan J, Doron B, Goloviznina N A, Lapidus J, et al. (2015), AML. Sci Rep 5: 11295.
9. Kourembanas S (2015), Annu Rev Physiol 77: 13-27.
10. Manterola L, Guruceaga E, Gallego Perez-Larraya J, Gonzalez-Huarriz M, Jauregui P, et al. (2014), Neuro Oncol 16: 520-527.
11. Munson P, Shukla A (2015), Medicines (Basel) 2: 310-327.
12. Ogata-Kawata H, Izumiya M, Kurioka D, Honma Y, Yamada Y, et al. (2014), PLoS One 9: e92921.
13. Properzi F, Logozzi M, Fais S (2013), Biomark Med 7: 769-778.
14. Taylor D D, Gercel-Taylor C (2008), Gynecol Oncol 110: 13-21.

We claim:

1. A particle size separation device, comprising:
a multi-membrane filter unit;
a resin matrix, wherein the resin matrix comprises an activated core and inactive shell, wherein only molecules smaller than about 200 nm are accessible to the activated core of the resin and become trapped upon contact with the core; and
wherein said multi-membrane filter unit comprises a series of membrane filters of decreasing size.

2. The particle size separation device of claim 1 wherein the series of membrane filters of decreasing size comprises an 80 µm filter membrane, a 10 µm filter membrane, and a 0.2 µm filter membrane.

3. The particle size separation device of claim 1 wherein a washer is included between each membrane filter in the series of membrane filters.

4. The particle size separation device of claim 1 further defined as a separation column.

5. The particle size separation device of claim 1 wherein the device is configured to remove particles having a size of greater than about 150 nm to about 200 nm from a sample.

6. The particle size separation device of claim 5 wherein the sample is a body fluid.

7. The particle size separation device of claim 6 wherein the body fluid is blood, saliva, breast milk, serum, plasma, or ascites fluid.

8. A method of selecting a molecule of interest having a defined particle size less than about 150 nm from a composition, said composition comprising particles having a size of greater than about 150 nm to about 200 nm, said method comprising:
Applying a sample to a separation column, said separation column comprising a series of filters of decreasing size, said decreasing size filters being a series of an 80 µm, 10 µm, and 0.2 µm filter membranes; said separation column further comprising a resin matrix comprising an activated core and inactive shell, wherein only molecules smaller than about 200 nm are accessible to the activated core of the resin and become trapped upon contact with the core; and
Collecting fractions of a buffer solution passed through the separation column, wherein said fractions correspond to particles within the sample having a particle size of from about 50 nm and about 150 nm;
wherein said collected fractions comprise less than about 25% particles of a size greater than about 150 nm to about 200 nm.

9. The method of claim 8 wherein the sample is a biological fluid.

10. The method of claim 9 wherein the biological fluid is blood, saliva, breast milk, serum, plasma, or ascites fluid.

11. The method of claim 8 wherein the particles within the sample having a particle size of from about 150 nm to about 200 nm are exosomes.

12. The method of claim 11 wherein the exosomes comprise a disease biomarker.

13. The method of claim 12 wherein the disease biomarker is a biomarker for tuberculosis.

14. The method of claim 8 wherein the buffer is a PBS buffer.

15. A particle size separation device, comprising:
a multi-membrane filter unit;
a resin matrix,
wherein said multi-membrane filter unit comprises a series of membrane filters of decreasing size; and
a washer is included between each membrane filter in the series of membrane filters.

16. The particle size separation device of claim 15 wherein the series of membrane filters of decreasing size comprises an 80 µm membrane filter, a 10 µm membrane filter, and a 0.2 µm filter membrane.

17. The particle size separation device of claim 15 further defined as a separation column.

18. The particle size separation device of claim 15 wherein the device is configured to remove particles having a size of greater than about 150 nm to about 200 nm from a sample.

19. The particle size separation device of claim 18 wherein the sample is a body fluid.

\* \* \* \* \*